United States Patent
Wilkins et al.

(10) Patent No.: US 11,957,593 B2
(45) Date of Patent: Apr. 16, 2024

(54) CEMENTLESS SCREW-IN-PEG FIXATION

(71) Applicant: Howmedica Osteonics Corp., Mahwah, NJ (US)

(72) Inventors: Sean Brian Wilkins, Hoboken, NJ (US); Kimberly Chan, River Vale, NJ (US); Sharon Sangermano, Red Bank, NJ (US); Carlos E. Collazo, Old Greenwich, CT (US); Wael Barsoum, Fort Lauderdale, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 211 days.

(21) Appl. No.: 17/550,242

(22) Filed: Dec. 14, 2021

(65) Prior Publication Data

US 2022/0202580 A1    Jun. 30, 2022

Related U.S. Application Data

(60) Provisional application No. 63/131,849, filed on Dec. 30, 2020.

(51) Int. Cl.
*A61F 2/38* (2006.01)
*A61F 2/30* (2006.01)

(52) U.S. Cl.
CPC .......... *A61F 2/389* (2013.01); *A61F 2/30771* (2013.01); *A61F 2002/30324* (2013.01); *A61F 2002/30863* (2013.01); *A61F 2002/30878* (2013.01)

(58) Field of Classification Search
CPC .... A61F 2002/3085; A61F 2002/30578; A61F 2002/30772; A61F 2002/30774; A61F 2002/30863; A61F 2002/30858; A61F 2002/30878; A61F 2/389; A61F 2/4081; A61F 2/44; A61F 2220/0008; A61F 2220/0016

See application file for complete search history.

(56) References Cited

U.S. PATENT DOCUMENTS

| | | | |
|---|---|---|---|
| 4,911,721 | A | 3/1990 | Andergaten 3 et al. |
| 5,879,389 | A | 3/1999 | Koshino |
| 6,102,951 | A | 8/2000 | Sutter et al. |
| 6,102,952 | A | 8/2000 | Koshino |
| 6,406,495 | B1 | 6/2002 | Schoch |

(Continued)

FOREIGN PATENT DOCUMENTS

| | | |
|---|---|---|
| CN | 111281620 A | 6/2020 |
| EP | 3593764 A1 | 1/2020 |
| WO | 2018017615 A1 | 1/2018 |

OTHER PUBLICATIONS

Extended European Search Report issued in Appln. No. 21215278.9 dated May 3, 2022.

(Continued)

*Primary Examiner* — Sarah W Aleman
(74) *Attorney, Agent, or Firm* — Lerner David LLP

(57) ABSTRACT

An orthopedic prosthesis includes a joint replacement portion that has a first side, a second side opposite the first side, and a screw hole that extends through the joint replacement portion from the first side and through the second side. The prosthesis also includes a peg that extends from the second side and that has a concave relief surface that partially defines the screw hole.

20 Claims, 4 Drawing Sheets

(56) References Cited

U.S. PATENT DOCUMENTS

| | | | |
|---|---|---|---|
| 7,462,199 | B2 | 12/2008 | Justin et al. |
| 7,578,850 | B2 | 8/2009 | Kuczynski et al. |
| 7,862,619 | B2 | 1/2011 | Clark |
| 8,048,161 | B2 | 11/2011 | Guederian et al. |
| 9,345,578 | B2 | 5/2016 | Collazo et al. |
| 9,381,085 | B2 | 7/2016 | Axelson, Jr. et al. |
| 9,445,909 | B2 * | 9/2016 | Cohen ................ A61B 17/1675 |
| 9,907,658 | B2 | 3/2018 | Cohen et al. |
| 9,937,058 | B2 | 4/2018 | Axelson, Jr. et al. |
| 9,949,837 | B2 | 4/2018 | Wang et al. |
| 10,194,963 | B2 | 2/2019 | Stalcup et al. |
| 10,231,840 | B2 | 3/2019 | Servidio |
| 10,722,374 | B2 | 7/2020 | Hodorek et al. |
| 2005/0015153 | A1 | 1/2005 | Goble et al. |
| 2005/0125068 | A1 | 6/2005 | Hozack et al. |
| 2012/0330431 | A1 | 12/2012 | Rolston |
| 2013/0218284 | A1 * | 8/2013 | Eickmann ................ A61F 2/389 |
| | | | 623/20.32 |
| 2016/0324649 | A1 | 11/2016 | Hodorek et al. |
| 2016/0367375 | A1 | 12/2016 | Boulris |
| 2017/0042690 | A1 | 2/2017 | Burkhead, Jr. et al. |
| 2018/0092747 | A1 | 4/2018 | Hopkins |
| 2020/0121465 | A1 | 4/2020 | Bloebaum et al. |
| 2020/0146835 | A1 | 5/2020 | Dhillon et al. |

OTHER PUBLICATIONS

Lecuire et al., Mid-term results of a new cementless hydroxyapatite coated anatomic unicompartmental knee arthroplasty, Eur J Orthop Surg Traumatol, Published online Feb. 2008, pp. 279-285, vol. 18.

Stryker, AxSOS 3® Titanium, Locking Plate System, Operative technique 4.0mm and 5.0mm compression plates, with SPS plating, 2019, 32 pages.

Zimmer Biomet, Oxford® Cementless Partial Knee, Brochure, 2016, 4 pages.

Unicompartmental knee prostheses, Web, Retrieved Nov. 5, 2020, <https://www.medicalexpo.com/medical-manufacturer/unicompartmental-knee-prosthesis-6603.html>, (17 screenshots provided).

Link Orthopaedics, Link Sled Prosthesis, Web, Retrieved Nov. 16, 2020, <https://www.linkorthopaedics.com/en/for-the-physician/products/knee-prostheses> (7 screenshots provided).

Amplitude, Surgical Technique with Conventional Instrumentation, UNI Score Unicompartmental Knee System, Brochure, 44 pages, downloaded from web on Nov. 16, 2020.

Euros, Europ UNI Fixe, Web, Retrieved Nov. 16, 2020, <https://www.euros.fr/products/?lang=en>, (18 screenshots provided).

Xnov, Xnov Kaps, Web, Retrieved Nov. 16, 2020, <https://www.xnov.com/EN/Product-knee.php> (7 screenshots provided).

\* cited by examiner

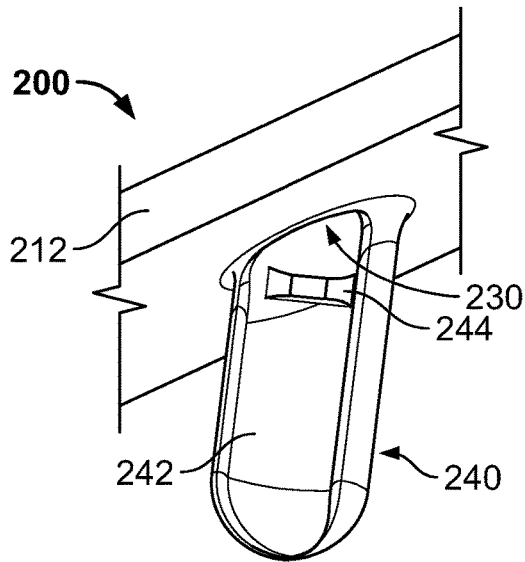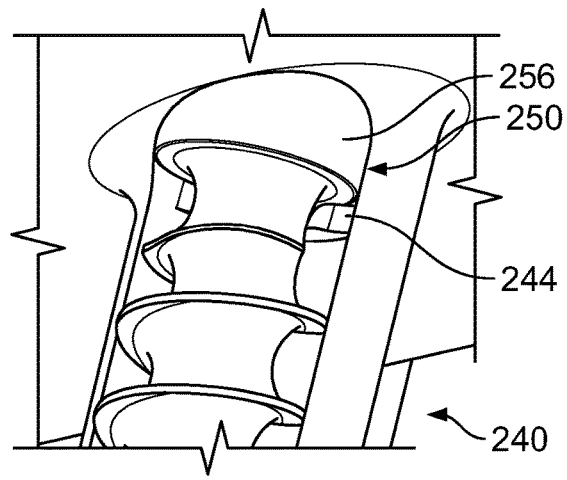
FIG. 3A  FIG. 3B
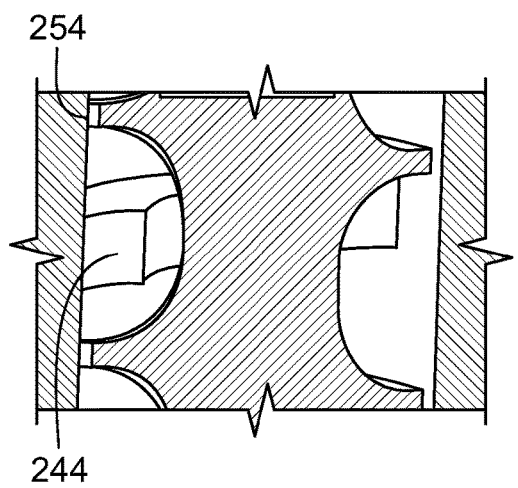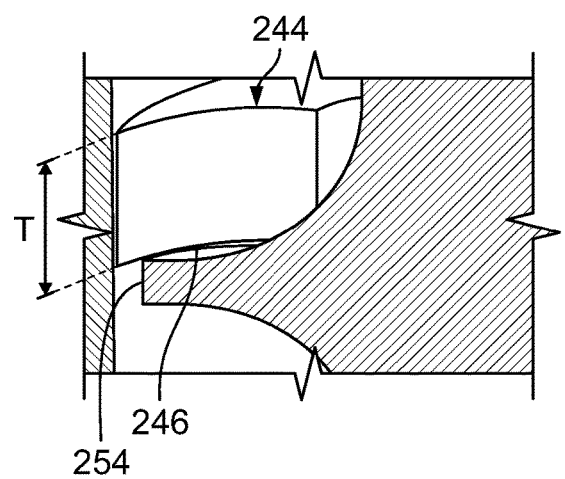
FIG. 3C  FIG. 3D

CEMENTLESS SCREW-IN-PEG FIXATION

CROSS-REFERENCE TO RELATED APPLICATIONS

The present application claims the benefit of the filing date of U.S. Provisional Application No. 63/131,849, filed Dec. 30, 2020, the disclosure of which is hereby incorporated herein by reference.

BACKGROUND OF THE INVENTION

Tibiofemoral joint disease is a condition commonly onset by osteoarthritis in which articular cartilage degenerates over time or is damaged through sudden trauma. This condition can result in bone-on-bone articulation which in some cases causes severe knee pain. A unicompartmental tibiofemoral joint replacement offers an alternative to a total joint replacement for patients with isolated tibiofemoral joint disease in either the lateral or medial tibiofemoral compartment, or who otherwise show no evidence of the disease present in the patellofemoral joint. In a unicompartmental tibiofemoral joint replacement, only the medial or lateral femur and tibia are replaced. This procedure provides pain relief while preserving significantly more bone than a total joint replacement.

Unicompartmental tibiofemoral joint implants have to withstand significant biomechanical forces experienced in-vivo to maintain sufficient fixation. Bone cement is commonly utilized as one means of implant fixation. Bone cement is typically applied to the interface between the implant and the bone and quickly cures to form a secure bond thereby providing strong initial fixation. However, bone cement has the propensity to break down over time resulting in component loosening that may lead to sudden failure and/or the need for a revision procedure.

Biological fixation provides an alternative to bone cement. Biological fixation is often achieved through the introduction of a porous implant surface to a resected bone surface. Over time, bone grows into the porous structure resulting in securement of the implant to the bone. However, biological fixation via bone ingrowth, while providing good long-term fixation, is often inadequate for initial fixation as it takes time for the necessary bone growth to occur. In this regard, implants may deploy other features to provide initial fixation in conjunction with porous structures. Such features may include pegs, keels, and the like which may help resist sliding or shifting of the implant relative to the bone.

However, despite these available options for initial fixation, it has been found that such options are often inadequate to resist the variety of forces unicondylar tibial components are subjected to during normal use. In particular, as a femur articulates in flexion relative to a tibia, femoral condyles roll posteriorly relative to tibial condyles so that the load applied by each femoral condyle also shifts posteriorly. Such shifting load applies a moment to the implant such that an anterior end of the implant has tendency to lift off of the tibial plateau potentially pulling the aforementioned mechanical features out of the bone. Therefore, further improvements are desirable.

BRIEF SUMMARY OF THE INVENTION

In one aspect of the present disclosure, an orthopedic prosthesis includes a joint replacement portion that has a first side, a second side opposite the first side, and a screw hole that extends through the joint replacement portion from the first side and through the second side. The prosthesis also includes a peg that extends from the second side and that has a concave relief surface that partially defines the screw hole.

Additionally, the orthopedic prosthesis may also include a screw that includes a shank, a head, and a helical thread that extends along at least a portion of a length of the shank. The peg may include a shelf that extends radially from the concave relief surface. The shelf may have a thickness less than a pitch of the screw thread. The peg may include a helical thread within the concave relief surface and may extend along at least a portion of a length thereof. The helical thread of the peg may be configured to threadedly engage the helical thread of the screw. The concave recess may define a cylindrical recess that extends radially inwardly from a periphery of the peg toward a longitudinal axis thereof. The screw hole may be counterbored so as to form a screw seat within the joint replacement portion. Also, the concave relief surface may partially define a cylinder coaxial with the screw hole. The screw hole may have a first radius of curvature and the concave relief surface may have a second radius of curvature equal to the first radius of curvature. The orthopedic prosthesis may also include a keel that extends from the bone contact side of the baseplate. The joint replacement portion may be a tibial baseplate.

In another aspect of the present disclosure, a tibial prosthesis includes a plate portion that has a first side, a second contact side opposite the first side, and a screw hole that extends from the first side through the second side. The screw hole has a central axis and a first radius of curvature. The prosthesis also includes a peg that extends from the second side and has longitudinal axis, a second radius of curvature, and a concave relief surface that extends along a length of the peg. The central axis and longitudinal axis are offset from each other a distance less than a sum of the first and second radii of curvature and the concave recess is aligned with the screw hole.

Additionally, the central axis and longitudinal axis may be parallel to each other. Also, the peg may be tilted such that an acute angle is formed between the longitudinal axis and second side of the plate portion. The peg may extend in a posterior direction. The concave relief surface may include a helical inner thread that may extend along a length of the concave recess. The peg may include a shelf that extends radially from the concave relief surface and toward the central axis. The screw hole may be counterbored so as to form a screw seat within the plate portion. The concave relief surface may partially define a cylinder coaxial with the central axis. The tibial prosthesis may also include a keel that extends from the second side of the plate portion. The tibial component may be a unicondylar tibial component.

In a further aspect of the present disclosure, a tibial prosthesis includes a plate portion that has a first side, a second side opposite the first side, and a screw hole. The screw hole extends from the first side through the second side and has a central axis. The prosthesis also includes a peg that extends from the second side of the plate portion. The screw hole intersects the peg so as to form a concave recess that extends along at least a portion of a length of the peg. The concave recess is defined by a partial surface of revolution that extends about the central axis of the screw hole.

BRIEF DESCRIPTION OF THE DRAWINGS

The features, aspects, and advantages of the present invention will become better understood with regard to the following description, appended claims, and accompanying drawings in which:

FIGS. 3A-3D are an enhanced partial perspective views of a peg, with and without a screw, of the tibial prosthesis of FIG. 1A according to a further embodiment of the present disclosure.

DETAILED DESCRIPTION

Figure 1A:
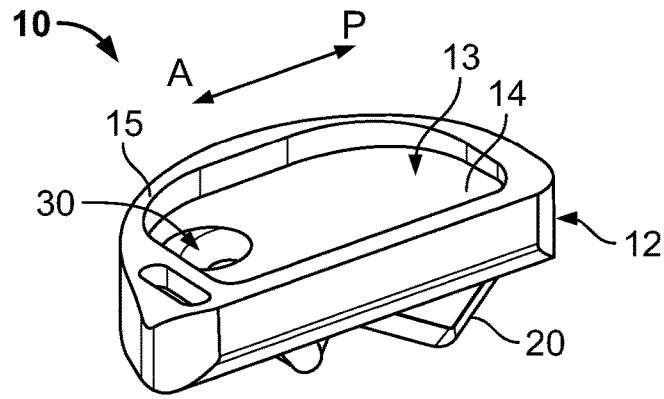
FIG. 1A is a top perspective view of a tibial prosthesis according to an embodiment of the present disclosure.
Figure 1B:
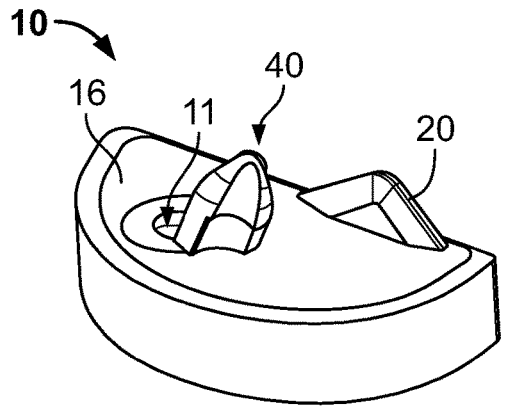
FIGS. 1B and 1C are bottom perspective views of the tibial prosthesis of FIG. 1A.
Figure 1C:
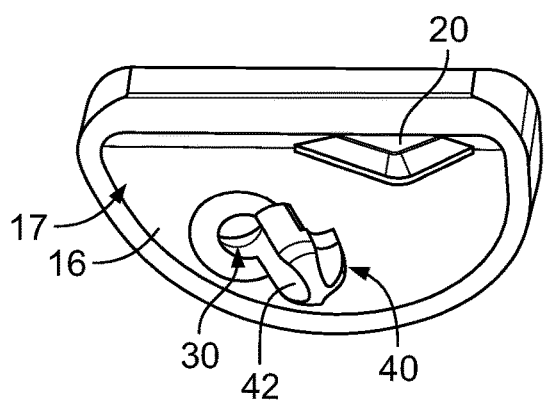
Figure 1D:
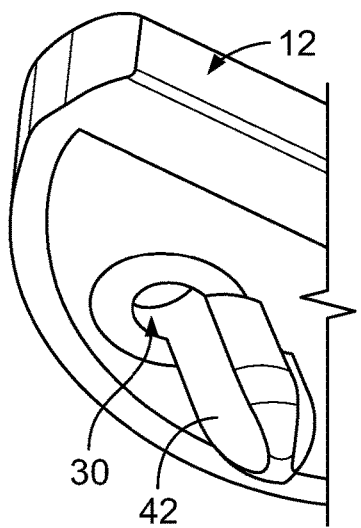
FIGS. 1D and 1E are enhanced partial perspective views of the tibial prosthesis of FIG. 1A.
Figure 1E:
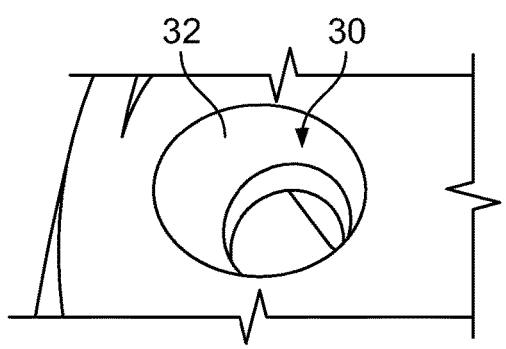

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that slight deviations from absolute are included within the scope of the term so modified.

FIGS. 1A-1H depict a tibial prosthesis 10 according to an embodiment of the present disclosure. Tibial prosthesis 10, as depicted, is a tibial baseplate component. Tibial baseplate component 10 may be a joint replacement portion of a partial knee prosthesis that may be comprised of a unicondylar femoral component (not shown), tibial baseplate component 10, and a tibial insert (not shown) connectable to tibial baseplate 10. Tibial baseplate 10 generally includes a plate portion 12, keel 20, screw hole 30, and peg 40.

Plate portion 12 has a first side or insert side 13 and a second side or bone contact side 17. Insert side 13 includes a tray which is formed of a depressed surface 14 bounded by a rim 15. Such tray is configured to receive a tibial insert which is typically a polymer element that has a condylar articular surface for articulation with a femoral component. Bone contact side 17 generally includes a bone interface surface 16 which is configured to contact a resected proximal tibia. As shown, interface surface 16 is planar and includes a porous structure for promoting bone ingrowth. In this regard, baseplate component 10 is configured to be implanted without bone cement.

Keel 20 extends from bone contact side 17 of plate portion 12 and is a fin-like structure that is triangular in shape. In the embodiment depicted, keel 20 is positioned nearer to a posterior end than an anterior end of baseplate component 10. Keel 20 is also oriented in an anteroposterior direction so that its narrowest cross-sectional dimension is transverse to the anteroposterior direction. Keel 20 also may include a porous structure for bone ingrowth and may be press-fit into bone and be self-broaching such that the bone does not need to be resected prior to its insertion.

Figure 1F:
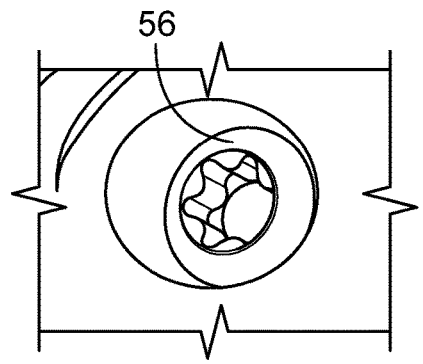
FIG. 1F is an enhanced partial perspective view of the tibial prosthesis of FIG. 1A including a screw.
Figure 1G:
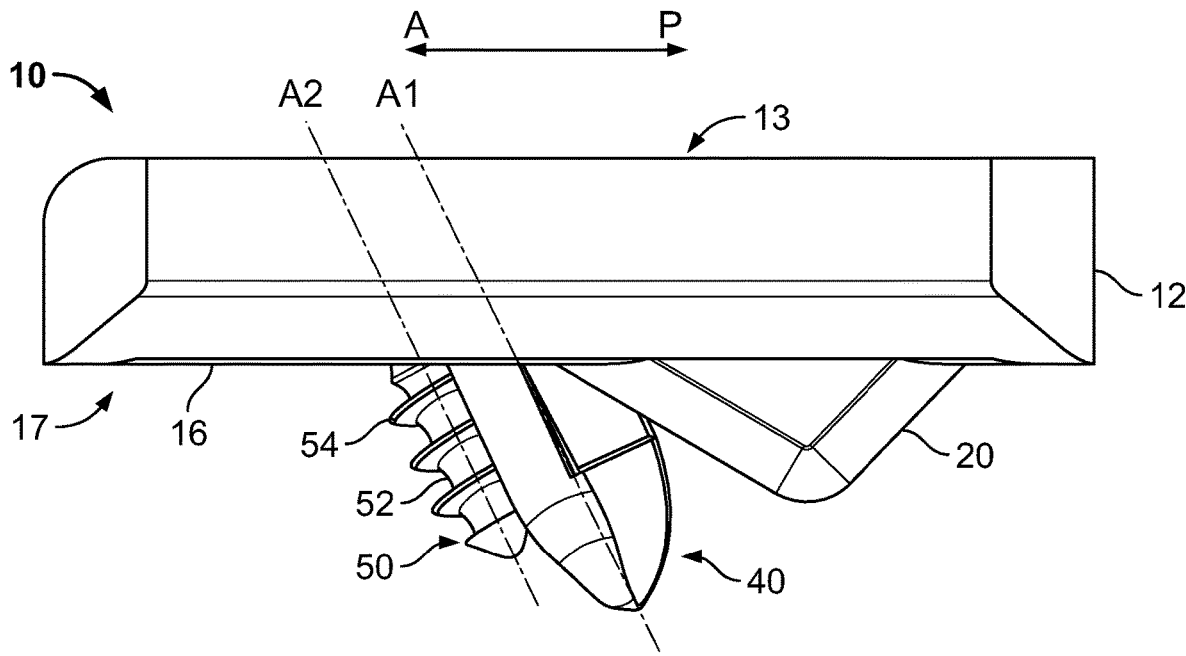
FIG. 1G is an elevational view of the tibial prosthesis of FIG. 1A including a screw.
Figure 1H:
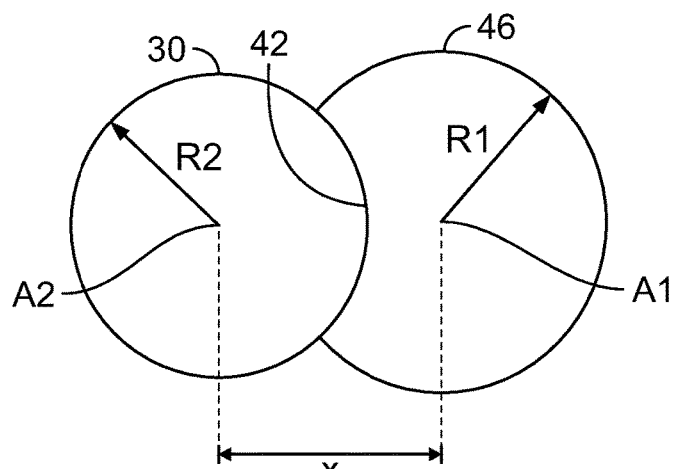
FIG. 1H is a schematic of a peg and screw hole of the tibial prosthesis of FIG. 1A.

Peg 40 extends from the bone contact side 17 and, in particular, from interface surface 16. Peg 40 includes a distal end remote from interface surface 16. The distal end may be configured to be inserted into a pilot hole in bone. However, in some embodiments the distal end may be configured to self-penetrate bone without a hole being pre-formed in the bone. Peg 40 has a longitudinal axis A1 that is preferably angled in a posterior direction so as to form an acute angle with interface surface 16. Thus, peg 40 is canted posteriorly. However, in some embodiments, peg 40 may not be canted and may instead be orthogonal relative to interface surface 16. Peg 40 has an outer periphery 46 which may be cylindrical, conical, or a combination of both cylindrical and conical. In this regard, peg 40 has a maximum diameter and a maximum radius or first radius R1, as best shown in FIG. 1H. Peg 40 further includes a concave relief surface 42 which defines a concave recess in the periphery 46.

A screw hole 30 extends through plate portion 12 from the insert side 13 to the bone contact side 17. Screw hole 30 has a hole-center which is coaxial with an axis A2 of the screw hole. Axis A2 of screw hole is angled relative to the interface surface 16 at an acute angle and is angled posteriorly. Screw hole 30, in the embodiment depicted, is a counterbore that has a maximum diameter at the insert side 13 of plate 12 and a minimum diameter at bone contact side 17 of plate 12 which forms a screw seat 32. This minimum diameter has a radius component, which is shown in FIG. 1H as a second radius R2. Screw hole 30 intersects the outer periphery 46 of peg 40 such that relief surface 42 partially defines the screw hole 30. In this regard, axis A2 of the screw hole 30 is coaxial with a center of curvature of relief surface 42, which is a cylindrical surface of revolution about such center of curvature. Second radius R2 is equal to a radius of relief surface 42. However, in some embodiments, these radii may differ. For example, the radius of relief surface 42 may be smaller than that the bone screw hole 30 so as to more closely conform to a threaded shank of the screw 50. As shown in FIG. 1G, axis A2 is parallel to the axis A1 of peg 40. These axes A1, A2 are offset from each other a distance X which is less than the sum of R1 and R2, as shown in FIG. 1H.

Screw 50 is a bone screw that has a threaded shank 52 and a screw head 56. As shown in FIGS. 1F and 1G, when screw 50 is inserted into screw opening 30, screw head 56 abuts screw seat 32, and threaded shank 52 is received in the concave recess of peg 40. Relief surface 42 partially conforms to thread 54 of screw 50. In this regard, peg 40 may be press-fit into the bone, such as by impacting peg 40 into a smaller diameter pre-formed bone hole or into the bone without a bone hole being pre-formed. Thereafter, screw 50 may be driven into the bone such that screw 50 pushes the peg 40 radially so as to further compress peg 40 against the bone thus providing both mechanical fixation by way of screw thread 54 and also by way of press-fit. Additionally, peg 40 may have a porous structure on its outer periphery to promote bone ingrowth. This bone ingrowth is further facilitated by the additional compression provided by screw 50.

Figure 2A:
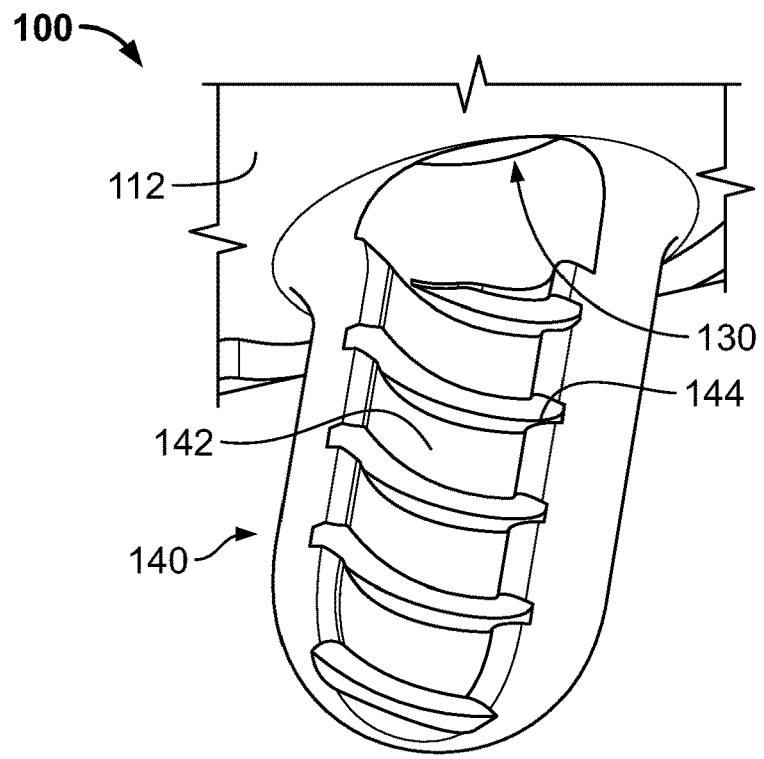
FIGS. 2A and 2B are an enhanced partial perspective views of a peg, with and without a screw, of the tibial prosthesis of FIG. 1A according to another embodiment of the present disclosure.
Figure 2B:
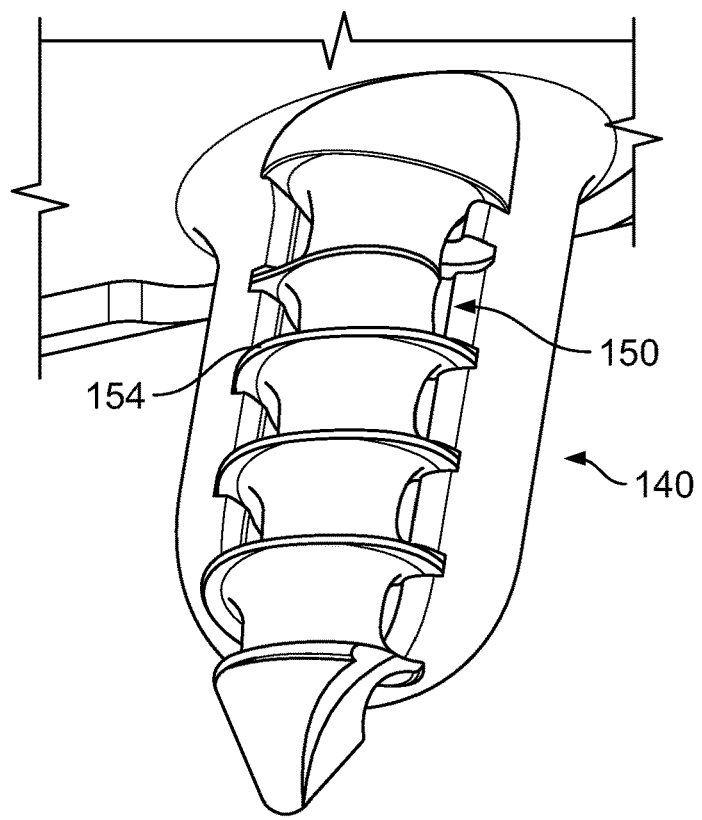

FIGS. 2A and 2B depict another embodiment baseplate 100 with an alternative peg and screw hole combination. For ease of review, like elements will be accorded like reference numerals to that of baseplate 10 but within the 100-series of numbers. In this regard, alternative baseplate 100 may include a keel and plate portion 112 that are the same as that described above with respect to baseplate 10. In addition, baseplate 100 may also include a screw hole 130 and peg 140 similarly situated to each other as peg 40 and screw hole 30. However, unlike with baseplate 10, peg 140 may include a female thread 144 that helically extends along relief surface 142. Thus, a bone screw, such as bone screw 140, extending through screw hole 130 would have its thread 154 threadedly engaged within thread 144 of peg 140. Thus, the radius of relief surface 142 may be smaller than that the minimum radius of screw hole 130 to ensure threaded engagement. While thread 154 is shown pre-formed in relief surface 142 of peg 140. It is also contemplated that relief surface 142 may be made of a material softer than that of screw thread 154 such that thread cuts into relief surface 142 as it is driven into the bone.

FIGS. 3A-3D depict yet another embodiment baseplate 200 with an alternative peg and screw hole combination. For ease of review, like elements will be accorded like reference numerals to that of baseplate 10 but within the 200-series of numbers. In this regard, alternative baseplate 200 may include a keel and plate portion 212 that are the same as keel 20 and plate portion 12 of baseplate 10. In addition, baseplate 200 may also include a screw hole 230 and peg 240 similarly situated to each other as peg 40 and screw hole 30. However, unlike with baseplate 10, peg 240 may have a rib or shelf 244 extending outwardly from relief surface 242. Additionally, screw hole 230 may not be counterbored and instead may have a uniform diameter. In this regard, shelf 244 may act as a screw seat for a screw head 256. As shown in FIGS. 3C and 3D, shelf 244 has a thickness T that is less than a thread pitch of thread 254. This allows shelf 244 to be disposed between thread 254 as screw 250 is threaded into hole 230 while acting as a back-out prevention mechanism. In other words, once screw 250 is threaded into bone and in screw hole 230, should such screw 250 attempt to back out of screw hole 230, thread 254 would impinge on an underside 246 of shelf 244 thereby preventing screw 250 from backing out.

Although the peg and screw hole combinations described above have been described in conjunction with a tibial baseplate, it should be understood that such peg and screw hole combination can be used with other joint replacement prostheses. For example, a glenoid baseplate, acetabular cup, femoral component, revision augments, and the like may also include a peg and a screw hole intersecting the peg so as to form a construction similar to that described herein. Additionally, it should be understood that, while only one peg and screw hole are shown in the exemplary embodiments herein, more than one combination of screw hole and peg may be provided. Additionally, more than one peg and/or screw hole by themselves may be provided in addition to the disclosed combination peg and screw hole.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic prosthesis, comprising:
   a joint replacement portion having a first side, a second side opposite the first side, and a screw hole extending through the joint replacement portion from the first side and through the second side; and
   a peg extending from the second side and having a concave relief surface that partially defines the screw hole, the concave relief surface being on an exterior surface of the peg and extending from the second side toward a free end of the peg.

2. The orthopedic prosthesis of claim 1, further comprising a screw having a shank, a head, and a helical thread extending along at least a portion of a length of the shank.

3. The orthopedic prosthesis of claim 2, wherein the peg includes a shelf extending radially from the concave relief surface, the shelf having a thickness less than a pitch of the screw thread.

4. The orthopedic prosthesis of claim 2, wherein the peg includes a helical thread within the concave relief surface and extending along at least a portion of a length thereof, the helical thread being configured to threadedly engage the helical thread of the screw.

5. The orthopedic prosthesis of claim 1, wherein the concave relief surface defines a cylindrical recess that extends radially inwardly from a periphery of the peg toward a longitudinal axis thereof.

6. The orthopedic prosthesis of claim 1, wherein the screw hole is counterbored so as to form a screw seat within the joint replacement portion.

7. The orthopedic prosthesis of claim 1, wherein the concave relief surface partially defines a cylinder coaxial with the screw hole.

8. The orthopedic prosthesis of claim 1, wherein the screw hole has a first radius of curvature and the concave relief surface has a second radius of curvature equal to the first radius of curvature.

9. The orthopedic prosthesis of claim 1, further comprising a keel extending from the bone contact side of the baseplate.

10. The orthopedic prosthesis of claim 1, wherein the joint replacement portion is a tibial baseplate.

11. A tibial prosthesis, comprising:
    a plate portion having a first side, a second contact side opposite the first side, and a screw hole extending from the first side through the second side, the screw hole having a central axis and a first radius of curvature; and
    a peg extending from the second side and having longitudinal axis, a second radius of curvature, and a concave relief surface extending along a length of the peg, wherein the central axis and longitudinal axis are offset from each other a distance less than a sum of the first and second radii of curvature and the concave recess is aligned with the screw hole.

12. The tibial prosthesis of claim 11, wherein the central axis and longitudinal axis are parallel to each other.

13. The tibial prosthesis of claim 11, wherein the peg is tilted such that an acute angle is formed between the longitudinal axis and second side of the plate portion.

14. The tibial prosthesis of claim 13, wherein the peg extends in a posterior direction.

15. The tibial prosthesis of claim 11, wherein the concave relief surface includes a helical inner thread extending along a length of the concave recess.

16. The tibial prosthesis of claim 11, wherein the peg includes a shelf extending radially from the concave relief surface and toward the central axis.

17. The tibial prosthesis of claim 11, wherein the screw hole is counterbored so as to form a screw seat within the plate portion.

18. The tibial prosthesis of claim 11, wherein the concave relief surface partially defines a cylinder coaxial with the central axis.

19. The tibial prosthesis of claim 11, further comprising a keel extending from the second side of the plate portion.

20. A tibial prosthesis, comprising:
a plate portion having a first side, a second side opposite the first side, and a screw hole, the screw hole extending from the first side through the second side and having a central axis; and
a peg extending from the second side of the plate portion,
wherein the screw hole intersects the peg so as to form a concave recess extending along at least a portion of a length of the peg from the second side toward a free end of the peg, the concave recess along the portion of the length being defined by a partial surface of revolution extending about the central axis of the screw hole and the concave recess being on an exterior surface of the peg.

\* \* \* \* \*